(12) United States Patent
Bajor et al.

(10) Patent No.: US 7,396,534 B2
(45) Date of Patent: Jul. 8, 2008

(54) **COSMETIC COMPOSITIONS CONTAINING *NIGROSPORA SPHAERICA* EXTRACTS**

(75) Inventors: John Steven Bajor, Ramsey, NJ (US); Michael James Barratt, Oak Ridge, NJ (US); Carol Annette Bosko, Oradell, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 728 days.

(21) Appl. No.: 10/843,489

(22) Filed: May 11, 2004

(65) Prior Publication Data

US 2005/0255056 A1 Nov. 17, 2005

(51) Int. Cl.
*A61K 36/06* (2006.01)
(52) U.S. Cl. .................................. 424/195.15; 424/401
(58) Field of Classification Search ................. 424/401, 424/195.15; 435/254.1
See application file for complete search history.

(56) References Cited

U.S. PATENT DOCUMENTS

| | | | |
|---|---|---|---|
| 3,616,247 A | 10/1971 | Hemming et al. | |
| 3,701,787 A | * 10/1972 | Evans et al. | ................. 549/292 |
| 4,284,720 A | 8/1981 | Petzoldt et al. | |
| 4,803,201 A | 2/1989 | Ratcliffe | |
| 4,845,027 A | 7/1989 | Calenoff et al. | |
| 4,963,356 A | 10/1990 | Calenoff et al. | |
| 5,039,710 A | 8/1991 | Ratcliffe | |

FOREIGN PATENT DOCUMENTS

WO 2004/065612 8/2004

OTHER PUBLICATIONS

Hardwooda, J. et al. "Nigrosporolide, a plant growth-inhibiting macrolide from the mould *Nigrospora sphaerica*", Natural Product Research, vol. 6, Issue 3, May 1995, 181-185.*
Printout www.atcc.org/SearchCatalogs/longview.cfm from The Global Bioresource Center™—Mar. 25, 2004, 9 pp.
Printout www.doctorfungus.org/thefungi/nigrospora.htm from doctor fungus™—Apr. 12, 2004, 3 pp.
Printout www.pagen.poznan.pl/news/abstract/a14.htm abstract from PAGEN Workshop, Apr. 4-5, 2003, 1 p.
International Search Report on Application No. PCT/EP2005/004494 dated Sep. 6, 2005.
Starratt et al., "Aggregation of the confused flour beetle, Tribolium confusum, elicited by mycelial constituents of the fungus *Nigrosporia sphaerica*", CA, 1971,m XP002202587, abstract.
Online, XP002342086, retrieved from www.alwaysnutrition.com/product, 2005.

* cited by examiner

*Primary Examiner*—Gina C. Yu
(74) *Attorney, Agent, or Firm*—Edward A. Squillante, Jr.; Ellen Plotkin

(57) ABSTRACT

Disclosed are extracts of *Nigrospora sphaerica* as cosmetic skin benefit agents, preferably as skin lightening agents alone or in combination with other skin benefit agents and together with a cosmetic vehicle. The inventive extracts, compositions and methods have effective skin lightening properties, may be easier to deliver to the skin, and are commercially available or cost-effective and available in nature.

15 Claims, No Drawings

COSMETIC COMPOSITIONS CONTAINING *NIGROSPORA SPHAERICA* EXTRACTS

FIELD OF THE INVENTION

The invention relates to compositions for topical application to human skin which compositions contain extracts of *Nigrospora sphaerica* and to methods of using the compositions for treatment and conditioning, and particularly for lightening, of skin.

BACKGROUND OF THE INVENTION

Many people are concerned with the degree of pigmentation of their skin. For example, people with age spots or freckles may wish such pigmented spots to be less pronounced. Others may wish to reduce the skin darkening caused by exposure to sunlight or to lighten their natural skin color. To meet this need, many attempts have been made to develop products that reduce the pigment production in the melanocytes. However, the substances identified thus far tend to have either low efficacy or undesirable side effects, such as, for example, toxicity or skin irritation. Therefore, there is a continuing need for new skin lightening agents, with improved overall effectiveness, as well as agents that lend themselves to ease of processing in their manufacture.

The present invention is based at least in part on the discovery that extracts of the fungus *Nigrospora sphaerica* have at least comparable and/or demonstrably better skin lightening activity than known skin lightening agents. The use of *Nigrospora sphaerica* for cosmetic applications has not heretofore been known.

SUMMARY OF THE INVENTION

The present invention alleviates the deficiencies of the prior art and includes, in part, a novel composition containing a pharmaceutically or cosmetically acceptable carrier and an extract of *Nigrospora spaerica*. The inventive compositions contain about 0.000001 to about 50% of extract of *Nigrospora sphaerica*, preferably, an organic solvent extract thereof. Preferably, the amount of the extract is about 0.00001% to about 10%, more preferably about 0.001% to about 7%, and even more preferably about 0.01% to about 5%, to attain optimum skin lightening activity at a minimum cost.

The present invention is based at least in part on the discovery that extracts of the fungus *Nigrospora sphaerica* have at least comparable skin and/or better skin lightening activity than known skin lightening agents.

In the preferred embodiment of the invention, further skin benefit agents may be included in the compositions and inventive method, such as alpha-hydroxy acids, beta-hydroxy acids, polyhydroxy acids, hydroquinone, t-butyl hydroquinone; Vitamin B and/or C derivatives; dioic acids, retinoids, resorcinol derivatives, betulinic acid, vanillic acid, betulinic acid, hydrolactin, and mixtures thereof. Organic and inorganic (e.g. micronized metal oxides) sunscreens may also be included. Organic sunscreens may include Benzophenone-3, Benzophenone-4, Benzophenone-8, Methoxycinnamate, Ethyl dihydroxypropyl-PABA, Glyceryl PABA, Homosalate, Methyl anthranilate, Octocrylene, Octyl dimethyl PABA, Octyl methoxycinnamate (PARSOL MCX), Octyl salicylate, PABA, 2-Phenylbenzimidazole-5-sulphonic acid, TEA salicylate, 3-(4-methylbenzylidene)-camphor, Benzophenone-1, Benzophenone-2, Benzophenone-6, Benzophenone-12, 4-Isopropyl dibenzoyl methane, Butyl methoxy dibenzoyl methane (PARSOL 1789), Etocrylene, and mixtures thereof.

The invention also includes methods of treating and conditioning skin by applying topically thereto the inventive compositions containing extracts of *Nigrospora sphaerica*. The invention also preferably includes a method of lightening the skin by applying thereto the inventive compositions. Compositions are useful in preventing or repairing such skin conditions as wrinkling, laxity, and photo damage.

The inventive compositions and methods have effective skin lightening properties, may be easier to deliver to the skin, and are cost-effective and available from natural sources.

DETAILED DESCRIPTION OF THE INVENTION

The present invention relates to compositions for topical application to human skin which compositions contain extracts of *Nigrospora sphaerica* and to methods of using the compositions for treatment and conditioning, and particularly for lightening, of skin.

*Nigrospora* is a filamentous dematiaceous fungus widely distributed in soil, decaying plants, and seeds. *Nigrospora* colonies are rapid growing, compact, woolly, at first white, becoming gray with black areas and a black reverse color. *Nigrospora sphaerica* produce conidiophores which forcibly discharge the conidia. Conidia are black, solitary, unicellular, slightly flattened horizontally, and have a thin equatorial germ slit. *Nigrospora sphaerica*, the best known species of the genus *Nigrospora*, may be found in the Hawaiian Islands and around the Pacific Ocean, among other places. The extracts of *Nigrospora sphaerica* suitable for use in present compositions are organic solvent extracts, e.g., alcoholic extracts (methanol) or ethyl acetate extracts.

According to the present invention, extracts of *Nigrospora sphaerica* must be presented in the composition in an amount of about 0.000001% to about 50% by weight of the composition. Preferably, the amount of the extract is about 0.00001% to about 10%, more preferably about 0.001% to about 7%, and even more preferably about 0.01% to about 5%, to attain optimum skin lightening activity at a minimum cost.

As used herein, the term "cosmetic composition" is intended to describe compositions for topical application to human skin.

As used herein, the term "comprising" means including, made up of, composed of, consisting and/or consisting essentially of.

The term "skin" as used herein includes the skin on the face, neck, chest, back, arms, axilla, hands, legs, and scalp.

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

It should be noted that in specifying any range of concentration, any particular upper concentration can be associated with any particular lower concentration.

*Nigrospora sphaerica*

The extracts according to the present invention are from a material of the Kingdom of fungi; Phylum of Ascomycota; Genus of *Nigrospora*; and Species of *sphaerica*. *Nigrospora sphaerica*, as used in accordance with the present invention, was harvested in the Hawaiian Islands and around the Pacific Ocean. After harvesting, the organisms are grown in a first culture medium, from which the specific strain is isolated and removed to be grown in a second culture medium. The *Nigrospora sphaerica* is then isolated from the second culture medium, followed by extraction. The culture and extraction techniques used in accordance with the present invention are those known or further developed by those skilled in the art of microbiology. The particular culture protocol under which the microorganism was grown and the extraction protocol that was used to prepare the extracts that were screened are set forth hereinbelow. The culture and extraction protocols are further translated below into detailed recipes for media preparation and methods of extraction.

Lead Collection Details

The following table contains information about the geographic location of collection, the media used to isolate the microorganism, and the morphological characteristics of the microorganism growing on agar isolation plates.

TABLE 1

| Location/Description | Collection Taken | Type Description | Salinity ppt | Recovery Media | Recovery Temp. | Isolation Media | Spore Formation | Fungal Texture |
|---|---|---|---|---|---|---|---|---|
| Hawaiian Islands: Coral reefs, rubble and lava tubes | Subtidal | Red | 36 | PDA (potato starch, dextrose) | 25 deg. C. | YPG (yeast, glucose, peptone) with SPC (soy, potato, carbohydrate) | FALSE | Dense tufts |

Fermentation Media for Fungal Cultures and Protocol

TABLE 2

| Media Component | Quantity |
|---|---|
| Sodium Citrate | 8 g |
| Cottonseed meal | 5 g |
| Mannitol | 5 g |
| Peptone | 4 g |
| L-arginine | 1.5 g |

Add Media components to 1 L seawater adjusted to pH=4.0±0.2.

Ferment in Stationary liquid for 16 days @25° C.

Extraction Protocol

Add approximately equal volume of HP-20 resin beads (DIAION brand, Mitsubishi, Japan) to the whole broth culture.

Shake for 2 hr.

Filter, wash twice with equal volume $H_2O$

Hold vacuum for 45 min. to dry

Extract residue with an equal volume of MeOH (methanol). Other suitable organic solvents include but are not limited to ethanol, acetone, ethyl acetate, chloroform, etc.

Filter, remove solvent.

Identification of Microorganisms

The identity of the microorganisms was confirmed to be *Nigrospora sphaerica* using the following procedure. Sample results, including fatty acid profiles and library matches were performed by Microbial ID Inc., Newark, Del.

Optional Skin Benefit Agents

Preferred cosmetic compositions are those suitable for the application to human skin according to the method of the present invention, which optionally, but preferably, include a skin benefit agent in addition to the inventive coumarin derived compounds.

Suitable additional skin benefit agents include anti-aging, wrinkle-reducing, skin whitening, anti-acne, and sebum reduction agents. Examples of these include alpha-hydroxy acids, beta-hydroxy acids, polyhydroxy acids, hydroquinone, t-butyl hydroquinone, Vitamic B and C derivatives, dioic acids, retinoids; betulinic acid; vanillic acid; allantoin, a placenta extract; hydrolactin; and resorcinol derivatives.

Cosmetically Acceptable Carrier

The cosmetically acceptable vehicle may act as a dilutant, dispersant or carrier for the skin benefit ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferentially oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$-$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterol esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), taurate polymer, cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums.

Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di- $C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

Optional Components

In the cosmetic compositions of the invention, there may be optionally added plasticizers; calamine; antioxidants; chelating agents; as well as sunscreens.

Other adjunct minor components may also be incorporated into the cosmetic compositions. These ingredients may include coloring agents, pigments, opacifiers, and perfumes. Amounts of these other adjunct minor components may range anywhere from 0.001% up to 20% by weight of the composition.

Sunscreens. For use as sunscreen, metal oxides may be used alone or in mixture and/or in combination with organic sunscreens. Examples of organic sunscreens include but are not limited those set forth in the table below.

The amount of the organic sunscreens in the cosmetic composition is preferably in the range of about 0.1 wt % to about 10 wt %, more preferably about 1 wt % to 5 wt %. Preferred organic sunscreens are PARSOL MCX and Parsol 1789, due to their effectiveness and commercial availability.

TABLE 3

| CTFA Name | Trade Name | Supplier |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |
| Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |

TABLE 3-continued

| CTFA Name | Trade Name | Supplier |
|---|---|---|
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

Use of the Composition

The fungal extracts, compositions and methods according to the invention are intended primarily as a personal care product for topical application to human skin, as well as to lighten the skin, to reduce the degree of pigmentation in the skin, or to even the skin tone.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The cosmetic composition of the invention can be formulated as a lotion having a viscosity of from 4,000 to 10,000 mPas, a fluid cream having a viscosity of from 10,000 to 20,000 mPas, or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. When the composition is a solid or semi-solid stick, it may be packaged in a suitable container for manually or mechanically pushing out or extruding the composition.

The invention accordingly also provides a closed container containing a cosmetically acceptable composition as herein defined.

The following examples are by way of example, not by way of limitation, of the principles of the present invention, to illustrate the best mode of carrying out the invention.

EXAMPLE 1

This example illustrates reduction in new melanin synthesis using the inventive extracts of *Nigrospora sphaerica*.

The extracts of *Nigrospora shpaerica* used throughout the examples that follow were prepared in accordance with the procedures set forth hereinabove.

Organ Culture Method

Waste skin from 8-month old pigmented pigs was shaved to remove hairs and washed thoroughly to remove debris and reduce microbial content. The cleaned skin was then dermatomed to approximately 1-mm thickness×75-cm$^2$ and placed in tissue culture flasks containing Dulbecco's Modified Eagle's Medium (DMEM Cat#1188507) containing penicillin (100-units/ml), streptomycin (100-ug/ml), kanamycin (200-ug/ml), glutamine (2-mM), and fungizone (0.5-ug/ml). All flasks were incubated overnight at 37° C. in the presence of 5% carbon dioxide. This allowed the skin to equilibrate for 18 hours prior to the addition of melanin inhibitors. Areas of the skin that had scratches, erythema, or uneven pigmentation were discarded.

The following morning, the skin was punched into 4-mm diameter biopsies and transferred to a 96-well tissue culture plate. To each well containing a biopsy, 180-microliters of fresh DMEM containing penicillin (100-units/ml), streptomycin (100-ug/ml), glutamine (2-mM), hydrocortisone (100-μg/ml) and 0.4-μCi/ml $^{14}$C-thiouracil (Moravek Biochemicals) was added along with 20-microliters of natural extract. (Extracts were initially dissolved in DMSO, i.e., dimethyl sulfoxide, and diluted with phosphate buffered saline.) All plates were returned to the incubator for three days.

Following the three day incubation, excess unincorporated radiolabel was removed by washing the biopsies at room temperature two times with 0.1 M carbonate buffer at pH 10 for 30 minutes and 2 hours respectively using an automated plate washer. Biopsies were then bleached and dissolved by addition of 100-microliters of 1 N NaOH/3% $H_2O_2$ followed by incubation overnight at 60° C.

Once dry, 50-microliters of 2N-HCl was added to each well to re-dissolve/neutralize the samples followed by the addition of 220-microliters of scintillation cocktail (Packard MicroScint-40). Samples were mixed several times to ensure even dispersion, sealed, and assessed for radiolabel incorporation using a Packard TopCount scintillation counter. A reduction in radiolabel incorporation translates to a reduction in new melanin synthesis.

TABLE 4

| Treatment | Concentration | % Radiolabel Reduction* |
|---|---|---|
| *Nigrospora sphaerica* extract | 80 ug/ml | 45 |
|  | 8 ug/ml | 4 |
| Kojic Acid | 1.4 mg/ml (10 mM) | 56 |

*Statistically significant an p-value of less than 0.05 using students t-test.

EXAMPLE 2

MelanoDerm Tissue Model Method

A MelanoDerm tissue equivalent model (MEL-300 from Mat Tek, Ashland, Mass.) containing melanocytes obtained from dark skin individuals was utilized to confirm the results obtained in the pig organ culture. MelanoDerms were cultured as per the supplier instructions.

Medium was replaced every two days over a 14-day period and treatments including the natural extracts were added to the medium phase at a final concentration of 50 and 100-micrograms per ml. Positive control was included, i.e., kojic acid, which is a known skin lightening agent. During each medium change, a portion of the waste was analyzed for levels of lactate dehydrogenase as an indicator of cellular toxicity and stress. At no time was the level of lactate dehydrogenase above the vehicle control solvents (water or ethanol).

Determination of melanin content within each MelanoDerm was performed using the assay provided by the manufacturer. Each MelanoDerm was homogenized in 450-microliters of buffer (1% SDS, 0.05-mM EDTA, 10-mM Tris-HCl, pH 6.8) containing 20-microliters of Proteinase K (5 mg/ml) and incubated overnight at 45° C. The following day, 50-microliters of sodium carbonate (500-mM) and 10-microliters of hydrogen peroxide (30% solution) was added to each sample and incubated at 80° C. for 30 minutes and then cooled. The optical density of the top phase was determined (405-nm) following extraction of the sample with 100-microliters of chloroform:methanol (2:1) and centrifugation (10,000 g) for ten minutes. Optical density readings relative to the untreated or vehicle control (water or ethanol) were then calculated.

TABLE 5

MelanoDerm Skin Equivalent Model Results

| Treatment | Concentration | % Melanin Reduction |
|---|---|---|
| Kojic Acid | 14 micro-g/ml (100 uM) | 9.5 |
| *Nigrospora sphaerica* Extract | 50 ug/ml | 60.9* |
| | 100 ug/ml | 48.9* |

*Statistically significant an p-value of less than 0.05 using students t-test.

EXAMPLE 3

Cosmetic compositions within the scope of the invention were prepared.

A base formulation shown in the Table below was made by heating phase A ingredients to 70 to 85° C. with stirring. Phase B ingredients were heated in a separate container to 70 to 85° C. with stirring. Then, phase A was added into phase B while both phases were kept at 70 to 85° C. The mixture was stirred for at least 15 minutes at 70 to 85° C., then cooled.

TABLE 6

| Ingredients | a % wt. | b % wt. | Phase |
|---|---|---|---|
| Isostearyl Palmitate | 6.00 | 6.00 | A |
| C12-C15 Alkyl Octanoate | 3.00 | 3.00 | A |
| PEG-100 Stearate | 2.00 | 2.00 | A |
| Glyceryl Hydroxystearate | 1.50 | 1.50 | A |
| Stearyl Alcohol | 1.50 | 1.50 | A |
| Stearic acid | 3.00 | 4.00 | A |
| TEA, 99% | 1.20 | 1.20 | B |
| Dimethicone | 1.00 | 1.00 | A |
| Sorbitan Monostearate | 1.00 | 1.00 | A |
| Magnesium Aluminum Silicate | 0.60 | 0.60 | B |
| Vitamin E acetate | 0.10 | 0.10 | A |
| Cholesterol | 0.50 | 0.50 | A |
| Simethicone | 0.01 | 0.01 | B |
| Xanthan gum | 0.20 | 0.20 | B |
| Hydroxyethylcellulose | 0.50 | 0.50 | B |
| Propylparaben | 0.10 | 0.10 | B |
| Disodium EDTA | 0.05 | 0.05 | B |
| Butylated hydroxytoluene | 0.05 | 0.05 | B |
| *Nigrospora sphaerica* extract | 0.05 | 2.00 | B |
| Niacinamide | 1.00 | 1.00 | B |
| Metal oxide | 2.50 | 5.00 | B |
| Methylparaben | 0.15 | 0.15 | B |
| Water | BAL* | BAL* | B |
| Total | 100.00 | 100.00 | B |

*BAL means Balance.

EXAMPLE 4

An additional cosmetic composition within the scope of the invention was prepared as follows:

1. Heat Phase A to 80° C.
2. Heat Phase B to 75° C. in a separate container
3. Add B to A and mix with heat off for 30 min.
4. At 50° C. add Phase C and mix for 10 min.

TABLE 7

| Component | Wt % | Phase |
|---|---|---|
| water, DI | BALANCE | A |
| disodium EDTA | 0.05 | A |
| magnesium aluminum silicate | 0.6 | A |
| methyl paraben | 0.15 | A |
| simethicone | 0.01 | A |
| butylene glycol 1,3 | 3.0 | A |
| hydroxyethylcellulose | 0.5 | A |
| glycerine, USP | 2.0 | A |
| xanthan gum | 0.2 | A |
| triethanolamine | 1.2 | B |
| stearic acid | 3.0 | B |
| propyl paraben NF | 0.1 | B |
| glyceryl hydroxystearate | 1.5 | B |
| stearyl alcohol | 1.5 | B |
| isostearyl palmitate | 6.0 | B |
| C12-15 alcohols octanoate | 3.0 | B |
| dimethicone | 1.0 | B |
| cholesterol NF | 0.5 | B |
| sorbitan stearate | 1.0 | B |
| Micronized titanium dioxide | 5.0 | C |
| tocopheryl acetate | 0.1 | B |
| PEG-100 stearate | 2.0 | B |
| sodium stearoyl lactylate | 0.5 | B |
| hydroxycaprylic acid | 0.1 | C |
| *Nigrospora sphaerica* extract | 10.0 | C |
| PARSOL MCX | 2.4 | C |
| alpha-bisabolol | 0.2 | C |

EXAMPLES 5-12

A set of additional compositions were prepared within the scope of the present invention and are listed in the table below.

TABLE 8

| Ingredients | Phase | 5 acid soap base | 6 | 7 | 8 | 9 | 10 | 11 | 12 |
|---|---|---|---|---|---|---|---|---|---|
| Stearic acid | A | 17.9 | 17.9 | 17.9 | 17.9 | 17.9 | 17.9 | 17.9 | 17.9 |
| Sodium cetearyl sulfate* (emulsifier) | A | | 2.2 | | 1 | 1.5 | 2 | 3 | 2 |
| Myrj 59* (emulsifier) | A | | | 2 | 2 | 2 | 2 | 2 | 1 |
| Span 60* (emulsifiers) | A | | | 2 | 2 | 2 | 2 | 2 | 1 |
| *Nigrospora sphaerica* extract | B | 0.05 | 0.05 | 2.0 | 2.0 | 3.5 | 3.5 | 5.0 | 10.0 |
| Micronized Zinc Oxide | B | 2.50 | 5.00 | 5.00 | 2.50 | 2.50 | 5.00 | 2.50 | 5.00 |
| KOH, 22% (form in situ soap with stearic acid) | | 2.20 | | | | | | | |
| Octyl methoxycinnamate | | 2.50 | | | 2.50 | 2.50 | | 2.50 | |
| Water | B | BAL | BAL | BAL | BAL | BAL | BAL | BAL | BAL |
| Glycerin | B | 1 | 1 | 1 | 1 | 1 | 1 | 1 | 1 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic method of skin lightening comprising applying to the skin a composition comprising:
   a. about 0.000001 wt % to about 50 wt % of a *Nigrospora sphaerica* extract; and
   b. a cosmetically acceptable carrier.

2. The method of claim 1, wherein said composition further comprises a sunscreen.

3. The method of claim 2, wherein said sunscreen is a micronized metal oxide.

4. The method of claim 1, wherein said composition comprises about 0.00001% to about 10% of said extract.

5. The method of claim 1, wherein said composition comprises about 0.001% to about 7% of said extract.

6. The method of claim 1, wherein said extract comprises about 0.01% to about 5% of said composition.

7. The cosmetic method of claim 1, wherein said *Nigrospora sphaerica* extract is an organic solvent extract.

8. The cosmetic method according to claim 1, wherein said composition further comprises a skin benefit agent selected from the group consisting of alpha-hydroxy acids, beta-hydroxy acids, polyhydroxy acids, hydroquinone, t-butyl hydroquinone, Vitamin B and/or C derivatives, dioic acid, retinoids, resorcinol derivatives, vanillic acid, betulinic acid, hydrolactin, and mixtures thereof.

9. The cosmetic method of claim 1, wherein said composition further comprises an organic sunscreen selected from the group consisting of Benzophenone-3, Benzophenone-4, Benzophenone-8, Methoxycinnamate, Ethyl dihydroxypropyl-PABA, Glyceryl PABA, Homosalate, Methyl anthranilate, Octocrylene, Octyl dimethyl PABA, Octyl methoxycinnamate, Octyl salicylate, PABA, 2-Phenylbenzimidazole-5-sulphonic acid, TEA salicylate, 3-(4-methylbenzylidene)-camphor, Benzophenone-1, Benzophenone-2, Benzophenone-6, Benzophenone-12, 4-Isopropyl dibenzoyl methane, Butyl methoxy dibenzoyl methane, Etocrylene, and mixtures thereof.

10. A cosmetic composition comprising:
   a. about 0.000001 to about 50% of *Nigrospora sphaerica* extract. and
   a. a cosmetically acceptable carrier
   wherein said composition further comprises a skin benefit agent selected from the group consisting of alpha-hydroxy acids, beta-hydroxy acids, polyhydroxy acids, hydroquinone, t-butyl hydroquinone, Vitamin B and C derivatives, dioic acids, retinoids, resorcinol derivatives, vanillic acid, betulinic acid, hydrolactin, and mixtures thereof.

11. The cosmetic composition of claim 10, wherein said extract is an organic solvent extract of *Nigrospora spaerica*.

12. The cosmetic composition of claim 10, wherein said extract comprises about 0.00001% to about 10% of said composition.

13. The cosmetic composition of claim 10, wherein said extract comprises about 0.001% to about 7% of said composition.

14. The cosmetic composition of claim 10, wherein said extract comprises about 0.01% to about 5% of said composition.

15. The cosmetic composition of claim 10, wherein said composition further comprises an organic sunscreen selected from the group consisting of Benzophenone-3, Benzopherione-4, Benzophenone-8, Methoxycinnamate, Ethyl dihydroxypropyl-PABA, Glyceryl PABA, Homosalate, Methyl anthranilate, Octocrylene, Octyl dimethyl PABA, Octyl methoxycinnamate, Octyl salicylate, PABA, 2-Phenylbenzimidazoie-5-sulphonic acid, TEA salicylate, 3-(4-methylbenzylidene)-camphor, Benzophenone-1, Benzophenone-2, Benzophenone-6, Benzophenone-12, 4-Isopropyl dibenzoyl methane, Butyl methoxy dibenzoyl methane, Etocrylene, and mixtures thereof.

* * * * *